United States Patent [19]

Whitehurst

[11] 3,994,978

[45] Nov. 30, 1976

[54] HYDROFORMYLATION OF OLEFINS

[75] Inventor: Darrell Duayne Whitehurst, Titusville, N.J.

[73] Assignee: Mobil Oil Corporation, New York, N.Y.

[22] Filed: Oct. 7, 1974

[21] Appl. No.: 512,788

Related U.S. Application Data

[60] Division of Ser. No. 387,873, Aug. 13, 1972, Pat. No. 3,875,125, which is a continuation-in-part of Ser. No. 270,913, July 12, 1972, Pat. No. 3,785,968.

[52] U.S. Cl. .......................................... 260/604 HF
[51] Int. Cl.² .......................................... C07C 45/04
[58] Field of Search ............... 260/604 HF; 252/430

[56] References Cited

UNITED STATES PATENTS

| 3,578,609 | 5/1971 | Haag et al. ...................... 260/604 R |
| 3,824,221 | 7/1974 | Ragg ............................. 260/604 HF |

Primary Examiner—James O. Thomas, Jr.
Assistant Examiner—W. B. Lone
Attorney, Agent, or Firm—C. A. Huggett; M. G. Gilman; C. A. Malone

[57] ABSTRACT

A cross-linked polystyrene resin modified by the presence therein of chemically bound sulfur provides a highly selective sorbent for removal of heavy metal contaminants from liquids containing the same.

1 Claim, 3 Drawing Figures

U.S. Patent  Nov. 30, 1976  3,994,978
FIG.1
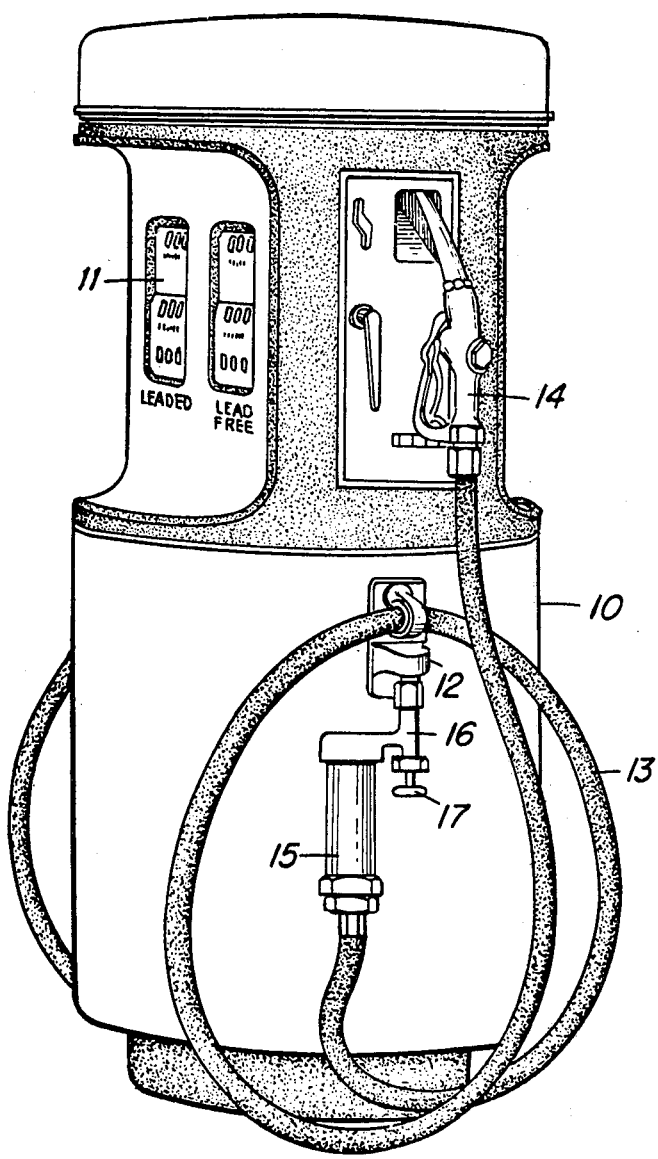
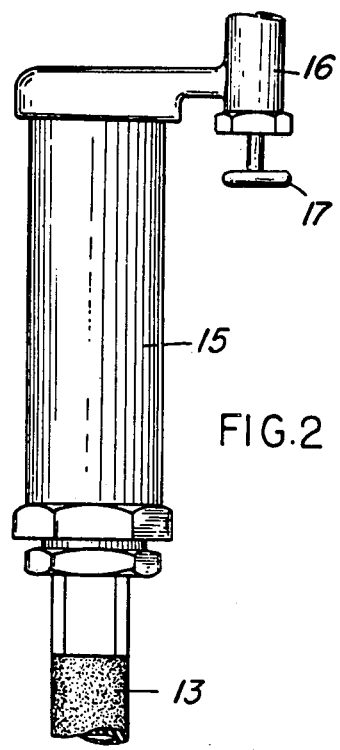
FIG.2
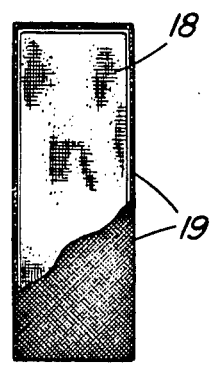
FIG.3

HYDROFORMYLATION OF OLEFINS

RELATED CASES

This application is a Division of Application Ser. No. 387,873, filed Aug. 13, 1973, now U.S. Pat. No. 3,875,125 which in turn is a continuation-in-part of U.S. Patent application No. 270,913, filed July 12, 1972, which issued Jan. 15, 1974 as U.S. Pat. No. 3,785,968.

BACKGROUND OF THE INVENTION

In many instances, it is desirable to effect removal of heavy metal contaminants from liquids. Thus, the presence of metals such as nickel, copper and iron, even in minute quantities, in hydrocarbon charge stocks conducted to catalytic cracking units are known to poison and shorten the life of the cracking catalyst with which such metal contaminated stocks come into contact.

It is also desirable to remove trace metals from lubricating oils or to recover soluble metal catalysts from reactor effluents. The removal of heavy metals such as mercury, silver, cadmium and the like from the water effluents of chemical or photographic plants is also highly desired from an ecological standpoint.

It is known that residues of alkyl lead from combustion of leaded gasoline tend to poison catalysts available for cleaning up automotive exhaust gas by oxidation of carbon monoxide and unburned hydrocarbons in the exhaust. Such poisoning severely shortens the useful life of exhaust combustion catalysts. It has heretofore been proposed that lead-free gasoline be supplied for use in automobiles equipped with emission control devices in the nature of combustion catalysts.

The normal network of petroleum product distribution involves railroad tank cars, pipelines, water borne tankers, tank trucks and bulk storage tanks. For commercial operation these are presently set up to handle different products. For example, the same pipeline will be used to convey a shipment of regular grade gasoline, premium grade gasoline, distillate fuel and other light liquid products in succession.

When leaded gasoline containing tetraethyl lead, tetramethyl lead or a mixture or transalkylation product of the two is contacted with the metal surfaces of transportation and storage facilities a significant amount of lead is left deposited in scale and on the metallic surfaces. Upon using the same facilities for lead-free gasoline, the latter product becomes contaminated to the extent of 0.07 grams of lead per gallon or more. These amounts of lead are sufficient to impair the life of exhaust emission catalysts.

It is accordingly highly desirable to provide selective means for effecting removal of heavy metal contaminant from liquids containing the same without interfering with or otherwise impairing the intended effectiveness of such liquids.

DESCRIPTION OF THE PRIOR ART

Techniques have heretofore been known for removal of dissolved or suspended heavy metal contaminants from liquid products.

In catalytic cracking operations, the use of guard chambers containing a variety of sorbents intended to remove heavy metal contaminant from the charge stock before contact is made with the cracking catalyst has been described.

Systems for removal of lead from gasoline have also been proposed. Presently known techniques require considerable time or are non-selective in effecting removal from the gasoline of those additives which are desired to be retained, such as anti-oxidants, anti-icing additives, metal passivators and the like.

One previously proposed system for removing lead is described in U.S. Pat. No. 2,368,261. There, acid acitivated clay such as bentonite which has been treated with hydrochloric or sulfuric acid is used. Leaded gasoline is percolated through the clay to remove 95% of the lead present. Acid activated clays will also remove the additives which are required for proper protection and functioning of automotive equipment.

Another approach is that described in U.S. Pat. No. 2,392,846. A five gallon lot of leaded gasoline is treated with 20 ml. of stannic chloride followed by addition of 100 grams of activated carbon. This results in decomposition of the tetraalkyl lead and adsorption on the activated carbon thus drastically reducing the lead content. The gasoline is removed from the activated carbon by decantation. This is a very slow process which permits the processing of about 35 gallons of gasoline per hour. Here also the additives desired to be retained will be adsorbed by the activated carbon.

Both the processes described in the cited prior patents depend for effectiveness on a chemical conversion of the tetraalkyl lead. The lead compounds can be reacted with such materials as halogens, halogen acids, metal halides, metal salts, sulfur dioxide, carboxylic acids, metals in the presence of hydrogen etc. The resulting decomposition products are not readily soluble in hydrocabons and hence are adsorbed on high surface adsorbents. This avoids the property of tetraalkyl leads which presents the greatest difficulty in this separation namely infinite solubility in hydrocarbons.

SUMMARY OF THE INVENTION

According to the present invention, there is provided a selective sorbent for lead and other heavy metal contaminants consisting essentially of a cross-linked polystyrene resin modified by the presence therein of chemically bound sulfur having an oxidation state of less than $^+6$. Preparation of such compositions involves reaction of readily available cross-linked polystyrene resins with elemental sulfur at elevated temperature in the presence of a substantially inert solvent, such as chlorinated hydrocarbon. The resultant porous solid contains a substantial quantity, generally between about 2 and about 30 weight percent, of chemically bound sulfur.

In one embodiment, lead free motor fuel may be handled through the normal distribution system of tankers, pipelines, bulk storage, etc., alternatively with leaded gasoline in a manner that suits the convenience of the operator in maximum utilization of capital facilities. Means are provided at the point of distribution, namely service station gasoline pumps, for selective removal of such amounts of tetraalkyl lead as may have been picked up by the fuel in storage or transit by passage of the fuel through a zone occupied by the sulfur-modified, crosslinked polystyrene resin described above. Thus, a cartridge of such composition may be installed at any point in the system for local storage and dispensing of lead-free gasoline at the service station.

In a preferred embodiment the cartridge is placed in the discharge line from the service station pump. This permits utilization of presently installed equipment and avoids the changes in design which would be required if the treating agent were installed in the fill pipe to the local storage tank, in the tank itself, in the suction line to the pump or within the pump housing, all of which alternatives are contemplated within the scope of the invention. A further alternative is placement of the lead removal cartridge in the automotive fuel system between the fuel tank of the vehicle and the carburetor. Flow rates are very small compared to those in bulk and retail distribution equipment, permitting long residence times and small volume cartridges.

BRIEF DESCRIPTION OF THE DRAWING

FIG. 1 of the drawings attached hereto represents a typical service station gasoline pump modified according to the present invention.

FIG. 2 is an enlarged view of the canister for containing the sulfur-modified, cross-linked polystyrene resin sorbent in the combination of FIG. 1.

FIG. 3 is a view in fragmentary section of a cartridge for containing the sulfur-modified, cross-linked polystyrene resin sorbent.

DESCRIPTION OF PREFERRED EMBODIMENTS

As shown in FIG. 1, a gasoline dispensing pump of conventional design includes a housing indicated generally at 10 within which are contained a motor driven pump and a metering device, not shown. The metering device drives, through suitable gearing, indicators within a panel 11 to report gasoline dispensed and price for the amount so dispensed. The fuel after passing through the metering device, is conducted to the outside of the housing through a pipe connection 12 and into a discharge hose 13 equipped with a valve nozzle 14.

The modification to conventional dispensing pumps is a canister 15 connected to the fuel discharge 12 by a pipe 16 provided with a valve for which the operating handle is shown at 17. Fuel from the pipe 16 is conducted to the top of canister 15 from which is passes through a cartridge of the sulfur-modified, cross-linked polystyrene resin sorbent and is thence discharged to hose 13 and nozzle 14.

A typical cartridge is shown in FIG. 3 as constituted by a gauze container 18 within a wire mesh supporting cage 19. Disposed within the container gauze 18 is a mass of the cross-linked polystyrene resin modified by the presence therein of chemically bound sulfur which characterizes this invention.

For the usual service station, a cartridge having a diameter of twenty-four inches and a length of twelve inches will be adequate to reduce the lead content to acceptable levels over a period of about one month. When it is desired to change the cartridge, valve 17 is closed, the hose 13 is drained and the canister 15 is removed by unthreading from the top portion thereof. It is thus a simple matter to replace the cartridge in a very short period of time and return the dispensing pump to duty.

The sulfur-modified, cross-linked polystyrene composition of this invention is suitably prepared by reacting a cross-linked polystyrene resin, preferably intrinsically porous with elemental sulfur at a temperature in the approximate range of 100° to 300° C. in the presence of a solvent inert with respect to sulfur, such as halogenated hydrocarbon solvents. The resultant solid, after removal of the solvent and extraction of any unreacted sulfur contains a substantial quantity, generally between about 2 and about 30 weight percent and preferably between about 5 and about 15 weight percent of chemically bound sulfur.

The polystyrene resin is preferably a solid, cross-linked, intrinsically porous material. It may be a copolymer of styrene with any of a number of co-monomers, for example, vinyl pyridine, acrylic derivatives, or substituted styrenes. The cross-linking agents may be any of those commonly used in commercial practices, for example, divinyl aromatics, acrylic esters, or other diolefins.

The reaction of the above polymers with elemental sulfur may be carried out in the presence of a halogenated hydrocarbon solvent such as chlorinated aromatic or aliphatic compounds, for example, chlorobenzene, ortho, meta, or paradichlorobenzene, any trichlorobenzene isomer, α-chloronaphthalene, 2,2'-dichlorobiphenyl, 1,1,1,2-tetrachloroethane, hexachlorocyclohexane or pentachlorocyclopentane. Reaction takes place at an elevated temperature, generally the reflux temperature of the particular solvent employed. The desired extent of reaction is usually complete after 2 to 100 hours, preferably between about 5 and about 40 hours.

The weight proportion of polystyrene resin to sulfur is generally in the range of 10:1 to 1:10. The reaction may be conducted in air, but is suitably carried out in an inert atmosphere, such as helium, argon, nitrogen, carbon dioxide, hydrogen sulfide or cabon monoxide.

After the reaction is completed, the solvent is removed from the solid reaction product by any suitable means such as filtration, centrifuging, or other means of separation. Any unreacted sulfur may be extracted by washing with a suitable solvent such as carbon disulfide, sulfur dioxide, liquid ammonia, aromatic hydrocarbons, halogenated hydrocarbons, such as dichloromethane, freon, diiodomethane or chloronated aromatics.

The resulting sulfur-modified, cross-linked polystyrene resin may be employed for removing heavy metal contaminant as described above. Such heavy metal removed may comprise one or more of the following: cobalt, iron, nickel, rhodium, platinum, palladium, lead, manganese, copper, mercury, gold, silver, iridium, cadmium and thallium. In some instances and circumstances, it is contemplated that the above metals, particularly precious metals, may be economically recovered by burning off the resin sorbent.

It has further been found that the above-described suflur-modified, cross-linked polystyrene resin in combination with a salt of a metal such as mercury, antinomy, tin, copper or silver and particularly these metals in their higher valence state such as the mercuric, antimonic, stannic or cupric state, affords enhanced removal of lead from gasoline. The amount of metal salt employed for said purpose is generally between about 5 and about 50 weight percent of the resin. Combination of metal salt and the sulfur-modified polystyrene resin may be accomplished in any feasible manner such as by impregnations of the latter with a solution of the metal salt or by depositing the metal salt on a porous support and physically admixing particles of the supported metal salt with particles of the sulfur-modified polystyrene resin, generally in a volume range of 1:10 to 10:1.

The following examples will serve to illustrate the sulfur-modified, cross-linked polystyrene resins of this invention and their use as selective sorbents for heavy metal contaminants.

EXAMPLE 1

The polymer used for this preparation was a standard macroreticular porous cross-linked polystyrene polymer manufactured by Rohm and Haas Company under the trade name "Amberlite" XAD-1.

The physical characteristics of this material, as received, are tabulated below:

| | |
|---|---|
| Solids (%) (Saturated with water) | 64.2 |
| Porosity (ml. pore/ml. bead) | 0.35 |
| Surface Area (m.²/g. - dry basis) | 100 |
| Effective Size (mm.) | 0.35 |
| Harmonic Mean Particle Size (mm.) | 0.44 |
| Average Pore Diameter (A) | 205 |
| True Wet Density (g.ml.) | 1.02 |
| Skeletal Density (g./ml.) | 1.06 |
| Bulk Density (lbs./ft.³) | 42.0 |
| (g./cc.) | 0.69 |

One liter of the polymer as received was cleaned by chromatographically washing with 5 liters of distilled water, 4 liters methanol, and 4 liters benzene. The adsorbed solvents were then removed by evaporation in a rotary evaporator at 70° C. in vacuo. The yield of dry material was 442 grams.

15.3 grams of this cleaned resin and 46 grams of sulfur were refluxed together in 300 ml. of 1,2,4-trichlorobenzene at a temperature of 220° C. for 64 hours.

Envolved $H_2S$ was trapped in a suitable adsorbent (Malcosorb and Aquasorb). The net gain in weight of the product so obtained was 4.2 grams. Elemental analysis of such product showed it to be composed, on a weight basis of the following:

| | |
|---|---|
| Carbon | 69.7% |
| Hydrogen | 3.6% |
| Sulfur | 21.2% |

EXAMPLE 2

The cleaned resin described in Example 1, in the amount of 100 grams, and 100 grams of sulfur were stirred together in 860 ml. of orthodichlorobenzene at reflux temperature and in helium atmosphere for 16 hours.

The orthodichlorobenzene solvent was removed from the resulting reaction product mixture while hot by filtration.

This solid product remaining was refluxed in approximately 1000 ml. of fresh orthodichlorobenzene for about one half hour.

The orthodichlorobenzene solvent was again removed from the solid remaining product, which was then rinsed with fresh orthodichlorobenzene.

The solid product was then soaked for 1 hour in approximately 1000 ml. of carbon disulfide. The carbon disulfide was removed from the solid by filtration and the solid product was rinsed with fresh carbon disulfide. Adhering carbon disulfide was then removed from the solid in a rotary evaporator at 70° C. and in vacuum. The sulfur containing resin's pH value was tested and found to be neutral. A NaCl solution was placed in a container with the sulfur containing resin and the mixture aggitated. The pH of the solution was again tested and found to be neutral.

The finished resin product, in the amount of 105 grams, analyzed, on a weight basis, as follows:

| | |
|---|---|
| Carbon | 89.74% |
| Hydrogen | 7.23% |
| Sulfur | 3.06% |

EXAMPLE 3

The cleaned resin described in Example 1, in the amount of 300 grams, and 500 grams of sulfur were stirred together in 1050 ml. of 1,2,4-trichlorobenzene and heated to reflux at 220° C. for 24 hours in a helium atmosphere.

The effluent gas from such reaction was passed through a mixture containing 400 grams of zinc nitrate, 2000 ml. of ammonium hydroxide and 2000 ml. of distilled water at 23° C.

Liquid in the resulting reaction product mixture was removed by filtration. The remaining solid product was washed with refluxing orthodichlorobenzene.

The latter was then removed by filtration and the remaining solid cooled to approximately 25° C, and washed extensively with carbon disulfide.

The washed solid was then dried on a rotary evaporator yielding 343.7 grams of product which analyzed on a weight basis, as follows:

| | |
|---|---|
| Carbon | 84.39% |
| Hydrogen | 6.32% |
| Sulfur | 8.30% |

EXAMPLE 4

The sulfur-containing resin product of Example 2 (approximately 0.5 gram) was contacted with approximately 3 ml. of a benzene solution containing about 10 milligrams of dicobalt octacarbonyl at room temperature.

Carbon monoxide evolution was noted and the solution became colorless. Infrared spectroscopy established that sorption of cobalt by the sulfur-containing resin had taken place.

EXAMPLE 5

Five (5) grams of the sulfur-containing resin product of Example 1, 150 ml. of orthodichlorobenzene and 0.9 gram of [tris-triphenylphosphine]rhodium chloride were refluxed together for 5 hours.

After cooling and filtering, the resin product was washed with approximately 500 ml. of carbon tetrachloride and dried overnight in a vacuum at 110° C. The dry weight of the product obtained was 5.45 grams.

Establishment of attachment of rhodium to the sulfur-containing resin was confirmed by the catalytic use of this material as follows:

Into a 300 c.c. stirred autoclave were charged 3 grams of the above resin product and 100 ml. of 1-hexene, together with carbon monoxide and hydrogen as a 1:1 volume mixture.

The autoclave contents were heated to reaction temperature and pressurized with the $H_2/CO$ mixture, also samples were taken periodically. Pressures were maintained between 700 and 1000 pounds and the temperature was 200° F. for 2 hours then raised to 245° for the duration of the reaction. Samples were taken at 2 hours and 19 hours. After 19 hours, the analysis of the product was found to be the following on a wt.% basis:

| | |
|---|---|
| Hexane | 10.9 |
| 1-Hexane | 46.1 |
| 2 & 3-Hexane | 53.0 |
| n-Heptanal | 6.6 |
| iso-Heptanals | 2.3 |

The above analysis indicates that the rhodium had been adsorbed and was catalytically active.

EXAMPLE 6

One (1) gram of the sulfur-containing resin product of Example 3, 15 ml. of benzene and enough rhodium carbonyl chloride to give a 0.5% coating to one gram of the resin product were contacted overnight at room temperature.

Benzene was then removed and the remaining product was washed lightly with 1-hexene.

Attachment of rhodium to the resin product was confirmed by catalytic use of this material in a manner similar to that described in Example 5.

Thus, into a 300 c.c. stirred autoclave were charged 1 gram of the above product and 100 ml. of 1-hexene, together with carbon monoxide and hydrogen as a 1:1 volume mixture.

The autoclave contents were heated to reaction temperature and pressurized with the $H_2/CO$ mixture. Pressures were maintained between 900 and 1000 psig and the temperature was 200° F. for 8 hours and then raised to 245° F. for 27 hours.

Analysis of a sample after this time showed that 2 and 3 hexenes, n- and iso-heptanal had been formed thus establishing that the rhodium had been adsorbed and was catalytically active.

Lead Removal Via Sulfur Modified Polystyrene

EXAMPLE 7

The resin product of Example 1 was used for the removal of lead from commercial gasoline. A commercial regular grade gasoline containing 2.41 g./gal. lead as tetraethyl and tetramethyl lead was contacted at about 25° C. with such resin product in a relative volume ratio of 10/1 respectively for a period of about 19 hours. Analysis of the gasoline at the end of this time showed that the lead level had been reduced to 0.9 g./gal. as a result of the described treatment.

EXAMPLE 8

The resin product of Example 3 was contacted with a benzene solution containing 23 g./l. of anhydrous stannic chloride and allowed to stand for about 2 hours. The solution was removed by filtration and the treated resin product washed with benzene. The resultant material was used to sorb lead from the same commercial gasoline as described in Example 7. At the end of the contact period (about 19 hours) the gasoline was found to have the lead content lowered to 0.38 g./gal.

EXAMPLE 9

The resin product described in Example 3 was used in conjunction with stannic chloride (about 30 wt. percent) on a separate support for effecting removal of lead from commercial gasoline similar to the one described in Example 7. The gasoline was treated at about 25° C. for 10 minutes employing 10 volumes of gasoline and 1 volume of the supported stannic chloride and 1 volume of the resin product of Example 3.

Results obtained are summarized below:

| | Untreated | Supported $SnCl_4$ | Supported $SnCl_4$ and Sulfur-Modified Resin |
|---|---|---|---|
| Lead in Gasoline g./gal. | 2.53 | 1.45 | 0.50 |

What is claimed is:
1. In a hydroformylation process comprising reacting carbon monoxide, hydrogen and $C_2$ to $C_{18}$ olefin at about 50°–200° C, 500–2500 psi, and a hydrogen to carbon monoxide ratio of .1-10 to 1; the improvement which comprises utilizing as a catalyst therefore, a cross-linked polystyrene resin modified by between about 2 and 30 weight percent of chemically bound sulfur having an oxidation state of less than +6 and which catalyst additionally contains about 0.1 to 10 weight percent of at least one member selected from the group consisting of rodium, cobalt and ruthenium, wherein said member is sorbed on the sulfur.

* * * * *